United States Patent [19]

van Boeckel et al.

[11] Patent Number: 5,071,969

[45] Date of Patent: Dec. 10, 1991

[54] SULPHATED K5 ANTIGEN AND SULPHATED K5 ANTIGEN FRAGMENTS

[75] Inventors: Constant A. A. van Boeckel, LX OSS; Gijsbert W. K. van Dedem, VX OSS; Neeltje A. Kraayeveld, CW DELFT, all of Netherlands

[73] Assignee: Akzo N.V., Arnhem, Netherlands

[21] Appl. No.: 320,341

[22] Filed: Mar. 8, 1989

[30] Foreign Application Priority Data

Mar. 10, 1988 [NL] Netherlands ................ 8800597

[51] Int. Cl.$^5$ ............... C08B 37/00; A61K 31/715
[52] U.S. Cl. ............... 536/1.1; 424/88; 424/92; 514/54; 514/56; 514/62; 536/54; 536/55.1
[58] Field of Search ........ 424/88, 92; 514/54, 514/56, 62; 536/1.1, 54, 55.1

[56] References Cited

U.S. PATENT DOCUMENTS

| | | | |
|---|---|---|---|
| 4,438,108 | 3/1984 | Sanders et al. | 536/123 |
| 4,510,132 | 4/1985 | Vaara | 514/11 |
| 4,719,202 | 1/1988 | van Boeckel et al. | 536/17.2 |
| 4,816,390 | 3/1989 | Kondo et al. | 436/518 |
| 4,841,041 | 6/1989 | van Boeckel et al. | 536/123 |

FOREIGN PATENT DOCUMENTS 0214879 3/1987 European Pat. Off. .
0240098 10/1987 European Pat. Off. .

OTHER PUBLICATIONS

J. Riesenfeld et al., "Biosynthesis of Heparin", Glyconjugate Journal, vol. 4, pp. 179–189 (1987).

*Primary Examiner*—Ronald W. Griffin
*Attorney, Agent, or Firm*—Donna Bobrowicz; William M. Blackstone

[57] ABSTRACT

The invention relates to sulphated K5 antigen and sulphated K5 antigen fragments containing at least 3 monosaccharide units and salts thereof, having interesting antiangiogenic and antitumor activities and a favorable ratio of the activities with respect to anticoagulant properties. In addition, the compounds can be used for the treatment of diseases caused by envelope viruses.

13 Claims, No Drawings

SULPHATED K5 ANTIGEN AND SULPHATED K5 ANTIGEN FRAGMENTS

The invention relates to K5 antigen derivatives and to fragments thereof, to methods of preparing such derivatives and fragments and to pharmaceutical preparations which contain such derivatives and/or fragments as active constituent.

K5 antigen occurs as a capsular polysaccharide in some *Escherichia coli* bacteria and has the repeating structure -$\beta$-D-glucuronyl-1,4-$\alpha$-N-acetyl-D-glucosaminyl-(1,4).

Surprisingly, it has now been found that sulphated K5 antigen and sulphated fragments thereof containing at least 3 monosaccharide units and salts thereof have inter alia interesting antiangiogenic and antitumour activities and, in addition, a favourable ratio of the activities with respect to anticoagulant properties.

The invention therefore relates to sulphated K5 antigen and sulphated K5 antigen fragments containing at least 3 monosaccharide units and salts thereof.

In this connection, "sulphated" is understood to mean that one or more of the OH groups in the K5 antigen or in fragments thereof, not including the OH groups in the COOH groups, is/are replaced by an $OSO_3H$ group.

The compounds according to the invention may contain a glucuronic acid or glucosamine as a terminal monosaccharide unit both at the reducing end and at the non-reducing end.

In the present application, fragments are understood to mean oligosaccharides and polysaccharides with the structure of the K5 antigen but having a lower molecular weight, with the proviso that they should also be understood to mean fragments which contain a glucuronic acid at the nonreducing end with a double bond between carbon atoms 4 and 5 (the 4-OH group is in that case missing in the glucuronic acid unit) and fragments which contain a glucuronic acid at the nonreducing end in which the 4-OH group is replaced by an H group and fragments which contain a glucosamine at the nonreducing end and fragments which contain an etherified OH group at the reducing end, such as, for example, a methoxy or ethoxy group, and fragments in which the aldehyde group at the anomeric end is reduced (0 replaced by OH).

In the given meaning, fragments may be prepared not only by fragmentation of the K5 antigen but also by synthesis from smaller saccharide units.

The number of monosaccharide units in the fragments is at least 3 and preferably at least 4 and still more preferably at least 5.

The molecular weight of the K5 antigen is $10^5$ $2.10^6$ dalton. If fully sulphated, the compounds according to the invention may therefore have a molecular weight of up to approximately $4.10^6$ dalton.

In the compounds according to the invention, all the amine groups in the glucosamine units are acetylated. The sulphate content is preferably on average at least 0.01 sulphate groups per monosaccharide unit and still more preferably, at least 0.25 and most preferably, 0.25-1. The maximum number of sulphate groups in the compounds according to the invention is equal to the number of OH groups in the corresponding unsulphated compounds, the OH groups in the COOH groups not being included.

Because the carboxyl and sulphate groups in the compounds according to the invention may occur in the ionized state in solution depending on the pH, the compounds according to the invention may also be prepared in the form of a salt in a manner known per se, such as, for example, by means of an ion exchanger in the $Na^+$ form. Salts which enjoy preference are salts suitable for pharmaceutical administration. The greatest preference is for sodium salts.

The K5 antigen can be isolated in a manner known per se, such as, for example, described in Eur. J. Biochem. 116(1984), 359-364. This method was further improved by arranging for the precipitation of the K5 antigen by means of a quaternary ammonium salt to be preceded by a treatment of the liquid containing the bacteria which contain the K5 antigen with 50-250 g of salt per liter of liquid. The invention therefore also relates to a method for isolating K5 antigen from a liquid containing bacteria which contain K5 antigen by precipitating the K5 antigen by means of a quaternary ammonium salt, and by extracting the K5 antigen by means of a salt from the precipitate obtained and subsequently purifying it, characterized in that the precipitation by means of a quaternary ammonium salt is preceded by a treatment with 50-250 g of another salt per liter of liquid. The pretreatment with salt is preferably carried out at 0°-10° C. for 0.5-5 hours. NaCl, KCl or $CaCl_2$ is preferably used as salt. The precipitation by means of a quaternary ammonium salt, the extraction of the K5 antigen from the precipitate by means of a salt and the purification may be carried out by known methods, for example by the method described in Eur. J. Biochem. 116(1984), 359-364. A further improvement was additionally found by treating the extract before the alcohol precipitation steps, between the alcohol precipitation steps, or immediately thereafter, with a hydroxide solution, for example an NaOH solution. The concentration of the hydroxide solution is 0.1-0.5 M; the quantity of solution used is 1-25 l. This treatment is carried out at 0°-30° C. for 2-48 hours. The phenol extraction described in the abovementioned article may be omitted. The improvements mentioned result in an improvement in yield of up to more than ten-fold.

The K5 antigen isolated is sulphated, preferably by means of an $(alkyl)_3N-SO_3$ complex, for example $(CH_3)_3N-SO_3$, $(C_2H_5)_3NSO_3$ or an $SO_3$ complex of an aromatic heterocyclic compound which has an N atom in the ring, such as, for example, pyridine —$SO_3$. The reaction is carried out at a temperature of 15°-80° C. The reaction time is 1 hour-40 days and is, just like the quantity of complex used, dependent on the degree of sulphation required. The reaction is preferably carried out in an organic solvent such as dimethyl formamide. If desired, the reaction with the complex may be repeated a number of times. The quantity of complex which is used may vary within wide limits but will, in general, lie between 0.01 and 5 mol per mol eq. of OH groups in the K5 antigen, the OH groups in the COOH groups not being included.

Sulphated K5 antigen fragments are prepared by fragmenting sulphated K5 antigen, by sulphating fragmented K5 antigen or by means of synthesis.

Sulphation of K5 antigen fragments takes place as has been described above for the sulphation of the K5 antigen.

The fragmentation of the K5 antigen is carried out in a manner known per se, for example, as described in FEMS Microbiology Letters 16(1983), 13-17. The fragmentation of sulphated K5 antigen can be carried out in an analogous manner. Surprisingly, it has now been found that the fragments thus obtained contain a glucuronic acid at the nonreducing end with a double bond between carbon atoms 4 and 5 and without an OH group on carbon atom 4. The invention therefore also relates to K5 antigen fragments with a glucuronic acid at the nonreducing end having a double bond between carbon atoms 4 and 5 and without an OH group on carbon atom 4. This double bond can, if required, be removed by means of hydrogenation or epoxidation, followed by reduction by methods known per se, or be removed by cleaving the unsaturated glucuronic acid, e.g. by treating the fragment with mercury (II) chloride.

Synthesis of sulphated K5 antigen fragments may be carried out as follows.

Starting from the compounds 1, 2 and 3 shown in the accompanying formula sheet, the compounds 2 and 3 are first of all reacted with each other, after which the product obtained is reacted with compound 1. These steps and the compounds 1 and 2 are known per se in the literature (see Example 4). Compound 3 was prepared as shown in Example 4. After saponification, sulphation, hydrogenation and selective N-acetylation by methods known per se (see Example 4), a sulphated K5 antigen fragment according to the invention is obtained from compound 4 (see Compound 5 of the formula sheet). As is evident from the formula sheet, the OAc and OBn group present in the starting products are eventually replaced by sulphate groups and hydroxyl groups respectively. If compounds in which one or more of the acetyl groups has been replaced by a phenylmethyl group and/or vice versa are used as the starting point, the sulphate groups will finally be situated in the position corresponding thereto. In this manner, sulphated K5 antigen fragments can be prepared in which it is precisely known where the sulphate groups are (will be) located in the sugar skeleton The final step in the preparation of such compounds is formed by selectively acetylating the sulphated K5 antigen fragment with amino groups in position 2 of the glucosamine units. Said acetylation is known per se (see Example 4). If desired, the fragments thus prepared may be sulphated further in the manner as described for the K5 antigen.

If compounds in which all the acetyl groups have been replaced by phenylmethyl groups are used as the starting point, after compound 4 according to the formula sheet has been obtained with the proviso that the acetyl groups in compound 4 have been replaced by phenylmethyl groups, saponification, hydrogenation, selective N-acetylation and sulphation are carried out in succession. Said sulphation is carried out as described for the K5 antigen.

The advantage of synthesizing compounds according to the invention lies in the fact that in this manner it is possible to determine beforehand where sulphate groups are provided on the sugar skeleton and that there is no dependence on the availability of bacteria containing K5 antigen. These considerations play a part, in particular, in the preparation of compounds according to the invention containing 3-9 monosaccharide units.

The compounds according to the invention, and in particular compounds according to the invention containing on average 0.25-1 sulphate group per monosaccharide unit exhibit an interesting antiangiogenic and antitumour activity and a favourable ratio of said activities with respect to anticoagulant properties. In addition, the compounds can be used for the treatment of diseases caused by envelope viruses such as, for example, herpes simplex virus, vesicular stomatitus virus, HIV type 1 and HIV type 2. The compounds show a potent inhibitory effect on syncitium formation, and cause a low metabolic burden.

The invention further relates to pharmaceutical preparations which contain sulphated K5 antigen and/or a sulphated K5 antigen fragment as active substance. The amount of active substance which is used lies per individual in general between 0.001 and 10 g per day and preferably between 0.002 and 5 g per day. The pharmaceutical preparation can be administered intravenously, intramuscularly, subcutaneously, orally, rectally or locally. Depending on the dosage form, the preparation contains the usual additives such as auxiliary substances, lubricants, antibacterial agents, antioxidants, binders, stabilizers etc. The pharmaceutical form may vary form tablet, powder and capsule to liquid, emulsion and cream, depending on the dosage form. The pharmaceutical preparations are prepared by galenical methods known per se.

The invention is explained in more detail on the basis of the following examples.

EXAMPLE 1

Production and isolation of K5 antigen

Medium A; composition in g/l:

| Peptone obtained from caseine | 1.7 |
|---|---|
| Peptone obtained from soya flour | 3 |
| Glucose | 2.5 |
| NaCl | 5 |
| $K_2HPO_4$ | 2.5 |
| pH | 7.3 |

Medium B; composition in g/l:

| $KH_2PO_4$ | 3 |
|---|---|
| $K_2HPO_4$ | 0.8 |
| Sodium citrate | 0.4 |
| $MgSO_4.7H_2O$ | 0.08 |
| $FeSO_4.7H_2O$ | 0.01 |
| Casamino acids | 20 |
| Yeast extract | 2 |
| Polypropylene glycol | 0.1 ml |
| Glucose | 40 |

Preculture of *E. coli* 010:K5:H4: 640 ml. Medium A was inoculated with a pure culture of *E. coli* 010:K5:H4 and subsequently incubation was carried out at 37° C. for 16 hours while stirring (120 r.p.m.).

16 l of medium B were inoculated with the preculture in a fermenter (18 l capacity).

Subsequently incubation was carried out at 37° C., pH 7.3 and 750 r.p.m. while supplying 6.4 l of air per minute for 7 hours. After heating to 90° C. for 5 min, the whole quantity was drawn off and heated for 30 min at 120° C. Subsequently, 2 kg of NaCl were added at 85° C. and stirred for 1½ hours at 0° C. This suspension was centrifuged (25 min, 7,000 g, 16° C.). The supernatant (14.5 l; pH=5.2; 125.4 mS/cm) was dialysed against pyrogen-free water (50 l of dialysate; pH=5.5; 34.1 mS/cm) and concentrated (40 l of permeate; pH=5.3; 25.5 mS/cm). The concentrate (1.3 l; pH=5.5; 24.1 mS/cm) was centrifuged (30 min, 27,000 g, 11° C.) and the supernatant obtained (1.25 l; pH=5.7; 25.8 mS/cm) was filtered through a coarse millipore filter, type AP-25. 6.5 l of ethanol were added to the filtrate. Subsequently, stirring was carried out for 30 min followed by centrifuging (30 min; 7,000 g; 15° C.). The sediment was dissolved in 3 l of demineralized water and stirred for 2½ days at 4° C. After adding 35 g of cetyltrimethylammonium bromide, the suspension was stirred for an hour and subsequently centrifuged (35 min; 27,000 g; 15° C.). The sediment obtained was dissolved in 1 l of 2.5 M NaCl and 8 l of ethanol was added to this solution. After stirring for one hour, the suspension was centrifuged (30 min; 7,000 g; 15° C.) and the sediment was dissolved and freeze-dried. The freezedried material was dissolved in 10 l of 0.3 M NaOH solution and stirred for 24 h at room temperature. Then the solution was neutralized with an HCl solution. Subsequently, 3 volumes of ethanol were added and after stirring for half an hour, the suspension was centrifuged (15 min; 7,000 g; 15° C.). The sediment was dissolved in 200 ml of water (2×distilled) and 600 ml of ethanol was added to this solution. After stirring for one night, the suspension was centrifuged and the sediment was dissolved in as little water as possible, dialysed (24 hours) and freezedried. Yield 11.4 g of K5 antigen, $[\alpha]_D^{20} = +80,4°$ (c=1, $H_2O$).

EXAMPLE 2

Fragmentation of K5 antigen

The preparation and isolation of K5 coliphage took place in accordance with Gupta et al, FEMS Microbiology Letters 14 (1982), 75-78, with the proviso that in the preparation of Loeb medium, the medium A already mentioned was used and that in the isolation, centrifugation was carried out instead of a treatment with chloroform/$NH_4SO_4$, and instead of using a caesium gradient, extraction with hexane, dialysis against phosphate buffer, filtration and filtration under sterile conditions were carried out in sequence.

4.7 g of K5 antigen prepared as in Example 1 were dissolved in 500 ml of $H_2O$ (doubly distilled). After dialysis of this solution against $H_2O$ (doubly distilled), 500 ml of the phage suspension obtained above were added and 48 h at 37° C. After cooling, filtration was carried out (8 μm filter) followed by passage through an ion exchanger (QAE-Zetaprep in cartridge housing, 1.4 l/h) Subsequently, 300 ml of $H_2O$ (doubly distilled) was passed through the ion exchanger. Then the K5 antigen fragments were eluted with NaCl solution (gradient 0→3 molar) and collected in 42 fractions. The fractions which contained fragments having a chain length of 4 sugar units were selected by means of extinction measurement at 234 nm, which provides a measure of the chain length of the fragments in the fractions, and subsequently combined. Subsequently, the fractions were evaporated down to 50 ml, desalted by means of a Sephadex G-10 column and freezedried. The extinction of the freezedried material at 234 nm and the uronic acid content were determined and an $H^1$-NMR spectrum recorded. These data revealed that the material was composed mainly of fragments having a chain length of 4 sugar units.

In an analogous manner, after incubating for 41 hours with a phage suspension, material having a chain length of mainly 6 sugar units, material having a chain length of mainly 8 sugar units and material having a chain length of mainly 10 sugar units were obtained The fragments thus prepared contained a glucuronic acid at the nonreducing end with a double bond between carbon atoms 4 and 5 (4-OH missing).

EXAMPLE 3

Sulphation of K5 antigen and K5 antigen fragments

K5 antigen (2.5 g) was dissolved in 300 ml of water and the solution was passed through a Dowex ion exchanger (50 WX-H4, H+ form, volume=90 cm³). This solution was adjusted to pH=8 by means of tetrabutylammonium hydroxide. Subsequently freezedrying was carried out, 400 ml of dry N,N-dimethyl formamide (DMF) were added and stirring was carried out for 1 day at 40° C. under nitrogen. After evaporating this suspension to dryness, 400 ml of dry DMF were added to the residue. After stirring for 4 hours under nitrogen at 40° C., the suspension was evaporated to dryness. 400 ml of dry DMF were added to the residue and the mixture was evaporated down after stirring for 4 hours at 30° C. under nitrogen. 500 ml of dry DMF were added to the residue. After the suspension had been stirred for half an hour at 30° C., 10.4 g of $(CH_3)_3NSO_3$ complex were added to the suspension. After having stirred the suspension for 3 ½ days under nitrogen at 35° C., $(CH_3)_3NSO_3$ complex (10.4 g) was added and the temperature was increased to 50° C. After stirring for 4 hours $(CH_3)_3NSO_3$ complex (10.4 g) was added and the temperature was reduced to 40° C. After stirring for 6 days, 550 ml of a saturated $NaHCO_3$ solution were added to the cooled (0° C.) reaction mixture. After stirring for 15 minutes, evaporating down and coevaporating twice with water, the residue was dried for 16 hours under vacuum. Subsequently, the crude product was dissolved in water, centrifuged and the supernatant was desalted until the conductivity of the dialysate was equivalent to that of tap water. The desalted solution was evaporated down and freezedried. The product was dissolved in a little water and passed through a Dowex column (50 WX-H4, Na+ form; volume=300 cm³). The eluate was dialysed against demineralized water by means of dialysing tube. Then the solution was made up to a volume of 1.8 l and filtered through a filter having pore diameter of 1.2 μm. After sterile filtration through a filter having a pore diameter of 0.2 μm, the filtrate was freezedried.

Yield 2.35 g of sulphated K5 antigen (average sulphate content 0.80 per sugar unit);
$[\alpha]_D^{20} = +65,3°$ (c=1, $H_2O$).

By repeating the sulphation method described above once and twice, sulphated K5 antigen was obtained having respectively a mean sulphate content per sugar unit of 1.15 and 1.25;
$[\alpha]_D^{20} = +46,5°$ (c=1, $H_2O$) and $+50,4°$ (c=1, $H_2O$) respectively.

The K5 antigen fragments obtained in Example 2 having 8, 6 and 4 sugar units were sulphated by the method below. Where the quantity used of a substance varied, the quantity used is given consecutively for 8, 6 and 4 sugar units.

K5 antigen fragment (57 mg, 490 mg, 9 mg) was dissolved in 300 ml of $H_2O$. This solution was passed through a Dowex ion exchanger (H+ form). The eluate was adjusted to pH=8 with tributylamine. After freezedrying, 25 ml, 80 ml, 5 ml of dry DMF were added and stirring was carried out for 1 day at 40° C. under nitrogen. After evaporating to dryness, 25 ml, 80 ml, 5 ml of dry DMF were added to the residue and stirring was carried out for 4 hours at 40° C. under nitrogen. After evaporating to dryness, 25 ml, 80 ml, 5 ml of dry DMF were again added to the residue and stirring was carried out for 4 hours at 30° C. under nitrogen. After evaporating to dryness, 25 ml, 1000 ml, 5 ml of dry DMF were added and stirring was carried out for half an hour at 50° C. under nitrogen. Subsequently, 237 mg, 2100 mg, 37 mg of $(CH_3)_3NSO_3$ complex were added to the suspension. After stirring for 27 hours, a second portion (237 mg, 2100 mg, 37 mg) of $(CH_3)_3NSO_3$ complex was added. After stirring for 3 days, the total quantity was cooled (0° C.) and a saturated $NaHCO_3$ solution (430 mg, 3500 mg, 60 mg) was added. After stirring for 15 min, evaporating down and coevaporating twice with water, the residue was dried for 16 hours under vacuum. Subsequently, the crude product was dissolved in a little water and desalted by means of Sephadex G-10. After evaporating down and freezedrying, the product was again dissolved in a little $H_2O$ and passed over a Dowex column ($Na^+$ form) The eluate was evaporated down to a small volume and again desalted by means of Sephadex G-10. Subsequently, the product was filtered (pore diameter 1.2 μm), sterile-filtered (pore diameter 0.2 μm) and freeze-dried.

Result 1. 79.4 mg of K5 antigen fragment containing 8 sugar units, average of 0.75 sulphate groups per sugar unit and $[\alpha]_D^{20} = +41.1°$ (c=1, $H_2O$).
2. 660 mg of K5 antigen fragment containing 6 sugar units, on average 1.6 sulphate groups per sugar unit and $[\alpha]_D^{20} = +32.2°$ (c=1, $H_2O$).
3. 23.8 mg of K5 antigen fragment containing 4 sugar units and on average 1.7 sulphate groups per sugar unit and $[\alpha]_D^{20} = +17.4°$ (c=1, $H_2O$).

EXAMPLE 4

Synthesis of sulphated K5 antigen fragments

The preparation of sulphated K5 antigen fragments is shown diagrammatically on the formula sheet. The compounds 1 and 2 shown there are known from J. Carbohydrate Chemistry 4 (1985), 293–321.

The compound 3 shown on the formula sheet is prepared by starting from compound 9 in Tetrahedron Letters 27(1986), 5889 ff. and 1-α-fluoro-2,3,4,6-tetra-O-acetylglucopyranose, which compound was prepared by dissolving 10 g of dry 1,2,3,4,6-penta-O-acetyl-glucopyranose in 40 ml of dry $CH_2Cl_2$ under nitrogen, cooling the mixture, then adding 22.4 ml (180 mmol) of HF-pyridine dropwise, stirring for 3 hours, washing with 20 ml of cold $NaHCO_3$ solution and 20 ml of cold NaCl solution, drying the organic layer, coevaporating with toluene and evaporating under vacuum. The starting products for the preparation of compound 3 according to the formula sheet were coupled to each other by the method described in Liebigs Ann Chem. 1984, pages 1826–1847. In this manner, methyl-0-3,6-di-O-benzyl-2-benzyloxycarbonylamino-2-deoxy-4-0-(2,3,4,6-tetra-O-acetyl-β-D-glucopyranosyl)-α-D-glucopyranoside was obtained. From this, compound 3 according to the formula sheet was obtained by using the steps for the preparation from compound 8 to 11b and from compound 22d to compound 23 as described in J. Carbohydrate Chem. 4 (1985), 293–321.

Compound 4 according to the formula sheet was prepared by reacting compounds 2 and 3 with each other and allowing compound 1 to react with the product obtained These steps were carried out as described for the preparation of the compounds 24b and 27b in J. Carbohydrate Chem. 4 (1985), 293–321.

The compound 4 according to the formula sheet was subsequently saponified, sulphated and hydrogenated as described in Carbohydrate Research 147 (1986), 121 ff. Finally, the compound thus obtained was selectively acetylated as in Methods of Carbohydrate Chem. 5 (1965), 407–409. In this manner, compound 5 according to the formula sheet was obtained. Yield 4.5 mg, $[\alpha]_D^{20} = +36.4°$ (c=1, $H_2O$).

Compound 5 was further sulphated by the method for sulphating K5 antigen fragments as described in Example 3. Yield 10 mg; the pentasaccharide contained 11 sulphate groups; $[\alpha]_D^{20} = +38.1°$ (c=1, $H_2O$).

In a similar manner to that described for compound 5, a pentasaccharide was prepared having an OH in position 3 of the centre glucosamine instead of an $OSO_3$ group. Yield 9.4 mg, $[\alpha]_D^{20} = +66.5°$ (c=1, $H_2O$).

We claim:

1. Sulphated K5 antigen and sulphated fragments thereof, said fragments comprising at least 3 monosaccharide units, and salts thereof.
2. Sulphated K5 antigen fragments according to claim 1, comprising at least 4 monosaccharide units and salts thereof.
3. Sulphated K5 antigen fragments according to claim 1, comprising at least 5 monosaccharide units and salts thereof.
4. Compounds according to claim 1, wherein the average number of sulphate groups per monosaccharide unit is at least 0.01.
5. Compounds according to claim 1, wherein the average number of sulphate groups per monosaccharide unit is 0.25–1.
6. Method for preparing compounds according to claim 1, characterized in that K5 antigen and/or K5 antigen fragments containing at least 3 sugar units are sulphated.
7. Method for preparing sulphated K5 antigen fragments according to claim 1, characterized in that sulphated K5 antigen is fragmented.
8. Method for preparing sulphated K5 antigen fragments according to claim 1, characterized in that a sulphated K5 antigen fragment containing amine groups in position 2 of the glucosamine unit is selectively acetylated.
9. Pharmaceutical preparation comprising at least one compound according to claim 1 in a therapeutically effective amount for antiangiogenic activity and an auxiliary substance selected from the group consisting of lubricants, antibacterial agents, antioxidants, binders and stabilizers.
10. K5 antigen fragment of claim 1 having a glucuronic acid at the nonreducing end thereof with a double bond between carbon atoms 4 and 5 of said glucuronic acid and without a hydroxyl group on carbon atom 4.
11. Method for isolating K5 antigen from a liquid containing bacteria which contain K5 antigen by precipitating the K5 antigen by means of a quaternary ammonium salt and by extracting the K5 antigen by means of a salt from the precipitate obtained and subsequently purifying it, characterized in that the precipitation by means of a quaternary ammonium salt is preceded by a treatment with 50–250 g of another salt per liter of liquid.
12. K5 antigen fragment of claim 1 having a glucuronic acid at the nonreducing end thereof, wherein the carbon atom 4-OH group of said glucuronic acid is replaced by a hydrogen atom.
13. K5 antigen fragment of claim 1 having a reduced aldehyde group at the anomeric end thereof.

* * * * *